United States Patent
Gittings

(10) Patent No.: US 9,597,125 B2
(45) Date of Patent: Mar. 21, 2017

(54) PROSTHETIC FACET AND FACET JOINT REPLACEMENT DEVICE

(75) Inventor: Darin C. Gittings, Sunnyvale, CA (US)

(73) Assignee: SPINAL KINETICS, INC., Sunnyvale, CA (US)

( * ) Notice: Subject to any disclaimer, the term of this patent is extended or adjusted under 35 U.S.C. 154(b) by 1250 days.

(21) Appl. No.: 12/927,208

(22) Filed: Nov. 8, 2010

(65) Prior Publication Data

US 2011/0093012 A1 Apr. 21, 2011

Related U.S. Application Data

(63) Continuation of application No. 11/540,044, filed on Sep. 29, 2006, now abandoned, which is a continuation-in-part of application No. 11/234,481, filed on Sep. 23, 2005.

(51) Int. Cl.
| | |
|---|---|
| *A61B 17/70* | (2006.01) |
| *A61F 2/44* | (2006.01) |
| *A61B 17/00* | (2006.01) |
| *A61F 2/30* | (2006.01) |

(52) U.S. Cl.
CPC ........ *A61B 17/7071* (2013.01); *A61F 2/4405* (2013.01); *A61B 17/7064* (2013.01); *A61B 2017/00867* (2013.01); *A61F 2/442* (2013.01); *A61F 2002/30563* (2013.01); *A61F 2002/30578* (2013.01); *A61F 2002/4495* (2013.01)

(58) Field of Classification Search
CPC .................................... A61B 17/7062–17/707
USPC .................... 606/246–249; 623/17.11–17.16
See application file for complete search history.

(56) References Cited

U.S. PATENT DOCUMENTS

| | | | | |
|---|---|---|---|---|
| 5,609,634 | A * | 3/1997 | Voydeville | 623/13.11 |
| 6,626,944 | B1 * | 9/2003 | Taylor | 623/17.16 |
| 7,238,204 | B2 * | 7/2007 | Le Couedic et al. | 623/17.11 |
| 2004/0106995 | A1 * | 6/2004 | Le Couedic et al. | 623/17.11 |
| 2006/0241610 | A1 * | 10/2006 | Lim et al. | 606/69 |
| 2006/0271044 | A1 * | 11/2006 | Petrini et al. | 606/61 |
| 2006/0293662 | A1 * | 12/2006 | Boyer et al. | 606/61 |
| 2007/0276500 | A1 * | 11/2007 | Zucherman et al. | 623/17.16 |

OTHER PUBLICATIONS

"Plate." Merriam Webster dictionary. http://www.merriam-webster.com/dictionary/plate accessed May 13, 2015.*

* cited by examiner

*Primary Examiner* — Jan Christopher Merene
*Assistant Examiner* — Steven Cotroneo
(74) *Attorney, Agent, or Firm* — E. Thomas Wheelock

(57) ABSTRACT

Spinal stabilization devices, systems, and methods are described. Foramenal spacers including a rigid member adapted to maintain the integrity of the foramenal space. Facet joint stabilizing members and prosthetic facet joints that augment or replace the native facet joint are also described. Lateral spinal stabilization systems that may be attached to the lateral surfaces of adjacent vertebral bodies are described. Also described are anterior spinal stabilization systems that are to be attached to the anterior surfaces of adjacent vertebral bodies. Several variations of dynamic spinal stabilization devices and systems are described. Each of the foregoing devices, systems, and methods may be used independently, in combination with the other devices, systems, and methods described herein, and/or in combination with prosthetic intervertebral discs.

6 Claims, 16 Drawing Sheets

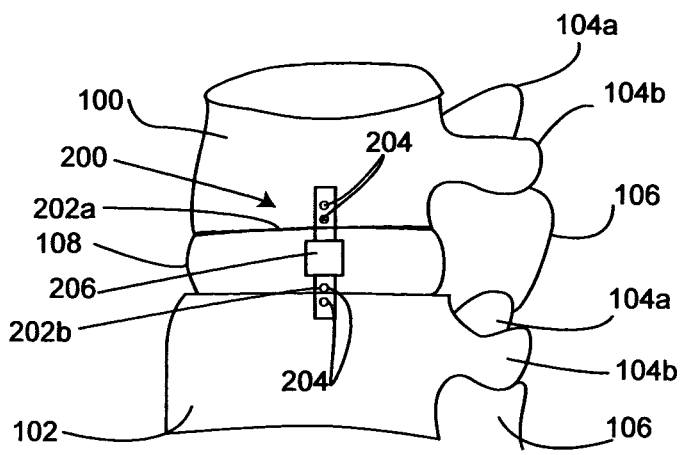
Fig. 8
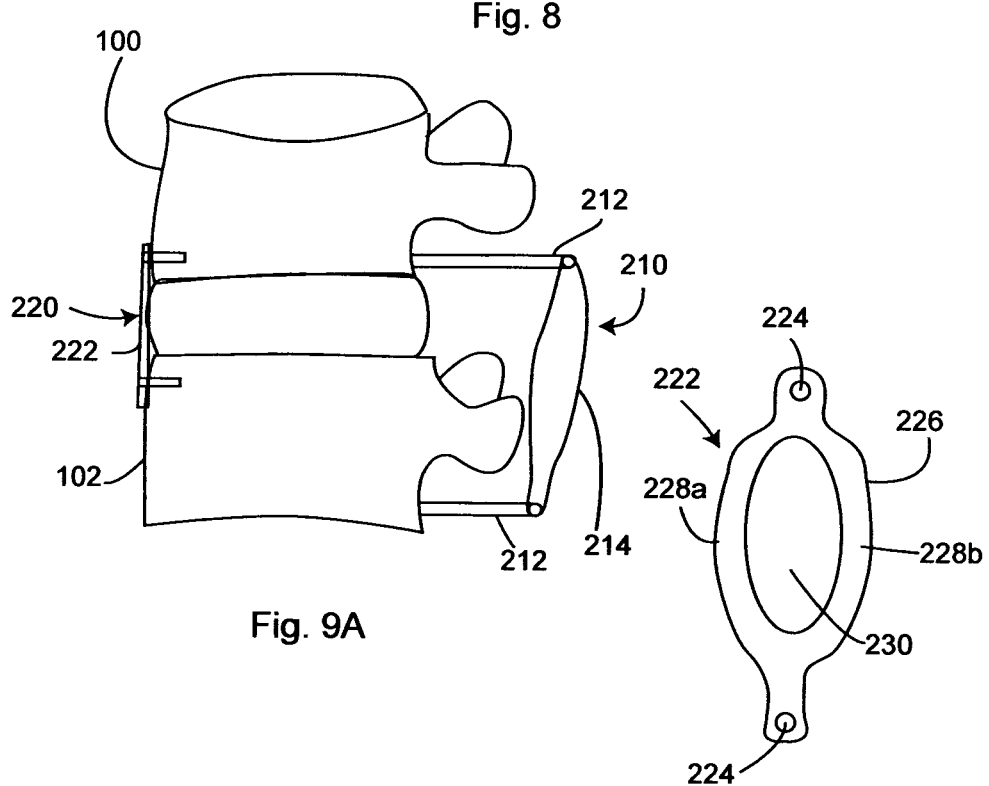
Fig. 9A
Fig. 9B

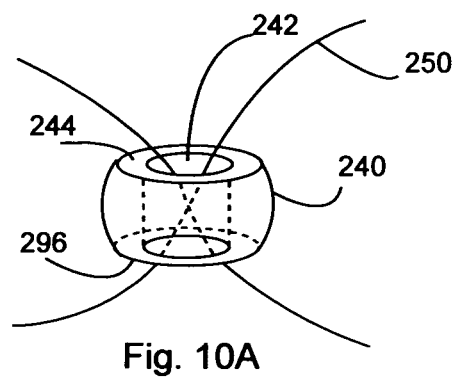
Fig. 10A
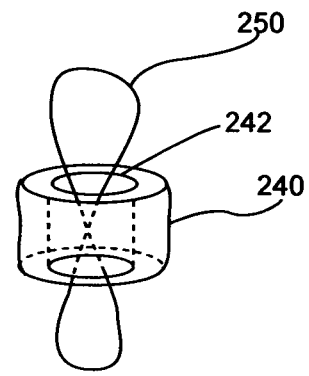
Fig. 10B₂
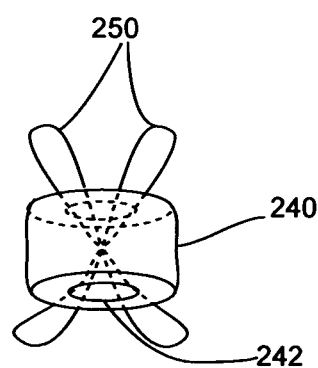
Fig. 10C₂

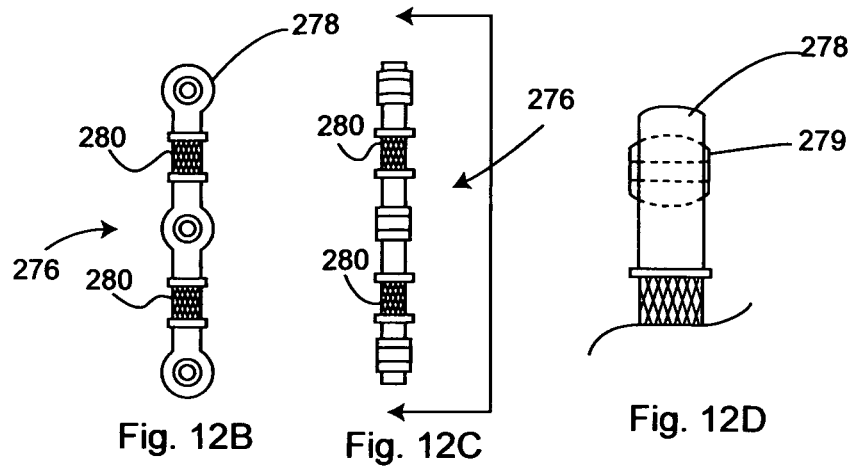
Fig. 12B  Fig. 12C  Fig. 12D
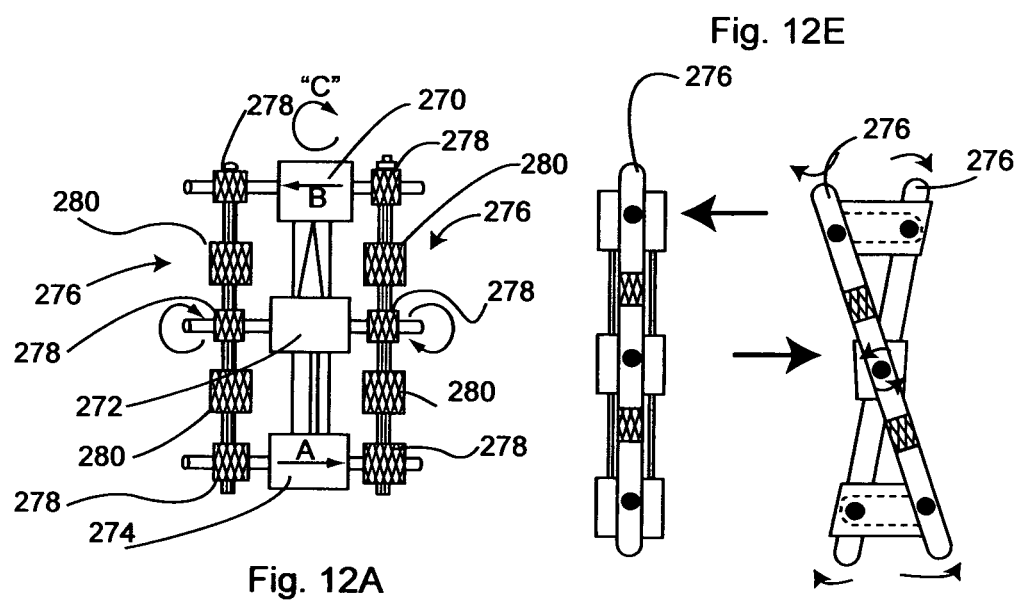
Fig. 12E
Fig. 12A
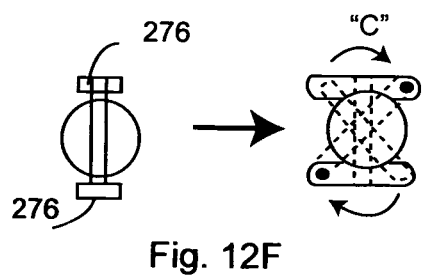
Fig. 12F

PROSTHETIC FACET AND FACET JOINT REPLACEMENT DEVICE

RELATED APPLICATIONS

This is a continuation-in-part of U.S. patent application Ser. No. 11/234,481, filed on Sep. 23, 2005, entitled "SPINAL STABILIZATION SYSTEMS AND METHODS" and a continuation of U.S. patent application Ser. No. 11/540,044, filed Sep. 29, 2006, entitled "PROSTHETIC FACET AND FACET JOINT REPLACEMENT DEVICE" the entirety of which are incorporated by reference.

BACKGROUND

The spine is comprised of twenty-four vertebrae that are stacked one upon the other to form the spinal column. The spine provides strength and support to allow the body to stand and to provide flexibility and motion. Each vertebra includes an opening through which the spinal cord passes enabling the spine to protect the spinal cord. The spinal cord includes thirty-one pairs of nerve roots that branch from either side of the spinal cord, extending through spaces between the vertebrae known as the neural foramen.

Between each pair of vertebrae is an intervertebral disc. The disc is composed of three component structures: (1) the nucleus pulposus; (2) the annulus fibrosus; and (3) the vertebral endplates. The disc serves several purposes, including absorbing shock, relieving friction, and handling pressure exerted between the superior and inferior vertebral bodies associated with the disc. The disc also absorbs stress between the vertebral bodies, which stress would otherwise lead to degeneration or fracture of the vertebral bodies.

Disorders of the spine are some of the costliest and most debilitating health problems facing the populations of the United States and the rest of the world, costing billions of dollars each year. Moreover, as those populations continue to age, the incidence of spinal disorders will continue to grow. Typical disorders include those caused by disease, trauma, genetic disorders, or other causes.

The state of the art includes a number of treatment options. Medicinal treatments, exercise, and physical therapy are typical conservative treatment options. Less conservative treatment options include surgical intervention, including microdiscectomy, kyphoplasty, laminectomy, dynamic stabilization, disc arthroplasty, and spinal fusion. Traditionally, these treatment options have been utilized in isolation, rather than in combination, and the most conservative of the treatment options utilized to provide a desired result.

U.S. Provisional Patent Application Ser. No. 60/713,671, entitled "Prosthetic Intervertebral Discs," ("the '671 application"), was filed Sep. 1, 2005, and is assigned to Spinal Kinetics, Inc., the assignee of the present application. The '671 application describes, inter alia, a treatment option that combines a prosthetic intervertebral disc with a dynamic stabilization system. The '671 application is incorporated by reference herein in its entirety.

In 1992, Panjabi introduced a model of a dynamic spinal stabilization system that describes the interaction between components providing stability in the spine. This model defined spinal instability in terms of a region of laxity around the neutral resting position of a spinal segment, identified as the "neutral zone." Panjabi, M M., "The stabilizing system of the spine. Part II. Neutral zone and instability hypothesis." J Spinal Disord 5 (4): 390-397, 1992b. There is some evidence that the neutral zone increases as a result of intervertebral disc degeneration, spinal injury, and spinal fixation. Id. Panjabi has subsequently described dynamic stabilization systems that provide increased mechanical support while the spine is in the neutral zone and decreased support as the spine moves away from the neutral zone. See United States Published Patent Application No. 2004/0236329, published Nov. 25, 2004, which is hereby incorporated by reference herein.

SUMMARY

We describe spinal stabilization components, systems, and methods for their use. The spinal stabilization components are suitable for use individually, together, or with other known spinal stabilization components and systems.

We describe foramenal spacers and methods for their use. The foramenal spacer includes a member having a size and shape suitable for insertion into the foramen located between a pair of adjacent vertebral bodies to prevent the pair of vertebral bodies from collapsing into one another, i.e., to maintain the interpedicular spacing between the adjacent vertebral bodies. The foramenal spacer may also include a passageway or include another member protecting the nerve root from being compressed or otherwise physically impacted as it traverses the foramen. The foramenal spacer may include an upper C-shaped member, a lower C-shaped member that interconnects with the upper C-shaped member, and an optional attachment member for attaching the upper C-shaped member to the lower C-shaped member. The upper C-shaped member is adapted to be attached to the pedicle of the superior vertebral body and to extend into the foramen defined by the pair of vertebral bodies, while the lower C-shaped member is adapted to be attached to the pedicle of the inferior vertebral body and to extend into the foramen defined by the pair of vertebral bodies. When attached together, the upper and lower C-shaped members define a passageway for passage of the nerve root. The attachment feature may comprise a tongue and groove mechanism, a snap-fit mechanism, or other suitable mechanism for attaching the upper and lower C-shaped member together. The upper C-shaped member and lower C-shaped member may each be provided with surfaces adapted to butt up against one another to form a butt-joint. The C-shaped members may be mated in such a way that they allow some travel (e.g., extension) relative to each other, such as that which may be required during flexion, extension and lateral bending, and maintain the patency of the passageway to allow passage of the nerve root.

Another of our foramenal spacers includes an upper segment and a lower segment. The upper segment is attachable to the pedicle of the superior vertebral body and extends into the foramen defined by a pair of vertebral bodies; the lower segment is attachable to the pedicle of the inferior vertebral body and also extends into the foramen defined by the pair of vertebral bodies. The interior surface of one of the upper segment or the lower segment and the external surface of the other of the upper segment or the lower segment define a pair of rounded, mating surfaces that together define a bearing structure that allows the upper segment to pivot relative to the lower segment. The upper segment and lower segment thereby act as a bearing having a center of rotation. Once the upper segment and lower segment are attached to the respective vertebral bodies and are engaged with one another, the foramenal spacer provides a supporting structure that also protects the nerve root traversing the foramen, and that allows the superior and inferior vertebral bodies to pivot relative to one another.

The foramenal spacer may be formed of a rigid biocompatible material, e.g., metal alloys such as stainless steel, nitinol, tantalum, or other metallic materials, or a rigid polymeric material. The foramenal spacer may be provided with an outer layer formed of a soft, conformable material (e.g., an elastomeric polymer such as polyurethane) that provides conformability with the foramen geometry and allows flexion, extension, and lateral bending of the spine. The foramenal spacer may include an inner liner formed of a soft and/or low-friction material to provide an atraumatic surface for passage of the nerve root.

We also describe devices, systems, and methods for facet joint augmentation and replacement. The devices and systems are intended to stabilize the spine and to increase the foramenal space to thereby reduce the likelihood of nerve root impingement. Stabilization and increase of foramenal space is accomplished by inserting a stabilizing member into the facet joint to restore the intra-foramenal distance. The stabilizing member may be made up of a structure that provides shock absorbance, cushioning, and support to the facet joint comprising, e.g., an encapsulated cushion. The stabilizing member may comprise a structure having a pair of endplates separated by a resilient core member.

In another variation, we describe facet joint implants. They are used in a procedure replacing some or all of the facets of each of the superior and inferior vertebral bodies. Our facet joint implant may include an upper prosthetic facet for attachment to the superior vertebral body, and a lower prosthetic facet for attachment to the inferior vertebral body. Each prosthetic facet is attached to its respective vertebral body by fasteners such as screws or the like. Each prosthetic facet joint of this design includes a pair of facing plates and a core member located between the pair of facing plates. The prosthetic facet is constructed and attached in a manner such that it closely mimics the functionality and performance of the natural facet joint.

We also describe a lateral spinal stabilization device. That lateral spinal stabilization device includes an upper attachment member and a lower attachment member for attaching to adjacent upper and lower vertebrae, respectively, and a stabilizing member connected to and extending between the upper and lower attachment members. The stabilizing member may comprise a damping mechanism or may comprise a pair of endplates separated by a resilient core member.

We also describe an anterior spinal stabilization device that is attached to the anterior surfaces of a pair of vertebrae that comprises a spring having a structure sufficient to carry a load after implantation. The anterior stabilization device may be implanted by way of a minimally invasive anterior approach, although posterior and lateral approaches are also suitable.

We also describe several dynamic stabilization devices are described. Each of the dynamic stabilization devices provides a combination of stabilizing forces to one or more spinal units to thereby assist in bearing and transferring loads. One dynamic stabilization device includes a posterior spacer member that is located between a pair of spinous processes on adjacent vertebral bodies. The posterior spacer may be formed of a generally compliant material and maintains spacing between the pair of adjacent vertebral bodies while allowing relative motion between the vertebral bodies. The posterior spacer may be in the form of a short cylinder or large bead-like structure, having a central through-hole to allow passage of one or more restrictor bands. The spacer itself may take other shapes or forms, however, depending upon the size and shape of the spinal treatment site.

This dynamic stabilization device may also include one or more elastic restrictor bands. The restrictor bands each have a size and shape allowing attachment to the spinous processes of adjacent vertebral bodies or attachment to the lamina of the adjacent bodies. Once linked to the posterior of the spine, the bands provide both stability and compliance. The performance properties of the bands may be varied by choice of materials, size of the bands, and by the routing of the restrictor bands between adjacent vertebral bodies. For example, restrictor bands that are oriented more vertically than diagonally will provide greater resistance to flexion of the spine, while a more diagonal orientation will provide additional resistance to torsional movements.

We also describe dynamic stabilization devices that may be adjusted post-operatively. For example, one variation of our dynamic stabilization device is made up of upper and lower attachment members for attachment to pedicles of adjacent vertebrae and one or more spring members extending between those attachment members. The spring member may be formed of a shape memory material, such as nitinol. Using a shape memory material such as nitinol allows alteration of the shape or length of the spring member by heating the spring, perhaps by applying an electric current to the spring. The electric current may be applied by placing leads against the spring member under X-ray or other guidance. A given spring member may be extended or contracted to provide greater or lesser load support, or to alter any other performance characteristic of the device.

We describe another spinal stabilization device that stabilizes the spine by transferring motions taking place (and correlated spinal loadings) in one spinal segment to an adjacent segment. Our spinal stabilization device transfers loads and reactions in the same manner as is done by the natural spinal segments operating properly. The spinal stabilization device is affixed to three adjoining vertebrae and allows for rotation of component linkage members about the center vertebral member, thereby allowing the functional transfer of load, either in compression or torsion, from one region of the spine to an adjacent vertebral region.

Another variation of our dynamic stabilization device includes a combination of an interspinous stabilization member and one or more pedicle based stabilization members. The pedicle based stabilization members function by biasing the pair of adjacent vertebral bodies apart, while the interspinous stabilization member functions by biasing together the spinous processes of the adjacent pair of vertebral bodies. The combined action of the interspinous member and the pedicle based members creates a moment arm that relieves pressure from the disc.

Another dynamic stabilization device is attached to a pair of adjacent vertebrae via their transverse processes and includes loading member extending between and interconnects the upper and lower transverse processes. Cooperating attachment members for the stabilization device may extend through the transverse processes into the vertebrae, or may be attached to the vertebrae adjacent to the transverse processes.

We describe dynamic stabilization devices that may be located externally of the patient's skin surface. Such stabilization members may be attached to a pair of adjacent vertebrae and extend between the vertebrae exterior of the patient. The device may be fully adjustable.

Such an external dynamic stabilization device may include a fill-type adjustment mechanism. Such device may be attached to the spinous process of an upper vertebral body and to the spinous process of a lower vertebral body and include a stabilization member extending between those vertebrae. The device may include adjustment members comprising fillable pots. As the pot is filled with a settable material, such as an epoxy, bone cement (e.g., containing polymethylmethacrylate (PMMA)), the functional length of the member is fixed.

Finally, we describe a dynamic stabilization device having an intervertebral spacer with an integrated stabilizing disc, the combined unit being situated between the spinous processes of adjacent vertebrae.

Each of the described devices, structures, and methods may be used independently, or in combinations of two or more. Indeed, each of the foregoing devices may be used in combination with a prosthetic intervertebral disc to obtain desired therapeutic results.

BRIEF DESCRIPTION OF THE FIGURES

The Figures are not necessarily drawn to scale. Some components and features have been exaggerated for clarity.

FIG. 8 is a lateral view of a pair of vertebral bodies having a lateral stabilization device implanted between them.

FIG. 9A is a lateral view of a pair of vertebral bodies having an anterior stabilization device and a posterior stabilization device.

FIG. 9B is an illustration of an anterior stabilization device.

FIG. 10A is an illustration of a spacer member.

FIGS. 10B-D are illustrations of posterior dynamic stabilization devices including a spacer member and restrictor bands both as implanted on the spine and isolated from the spine.

FIG. 12A is a posterior, schematic view of a dynamic stabilizer traversing two adjoining discs.

FIGS. 12B and 12C are, respectively, front and side views of one element of the dynamic stabilizer shown in FIG. 12A.

FIG. 12D shows the end of the element shown in FIGS. 12B and 12C.

FIGS. 12E to 12F show movement of the elements during rotation of the spine.

DESCRIPTION

Figure 1:
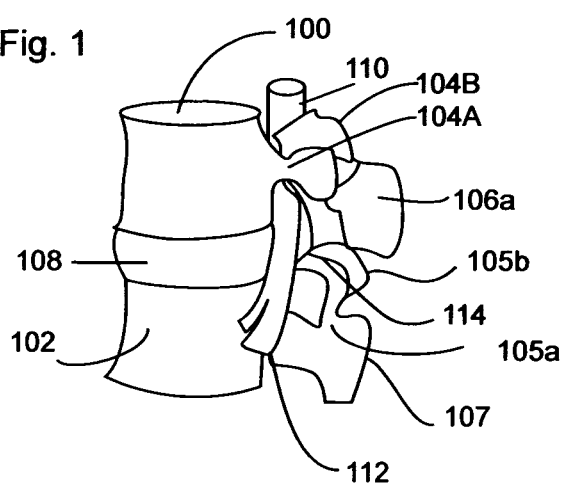
FIG. 1 is a lateral view of a pair of adjacent vertebral bodies, including representation of the foramen and nerve roots traversing the foramen.

FIG. 1 illustrates a pair of adjacent vertebrae, including a superior or upper vertebral body (100) and an inferior or lower vertebral body (102). Upper vertebral body (100) includes a pair of transverse processes (104a, 104b) and a spinous process (106) extending generally posteriorly. Lower vertebral body (102) includes a pair of transverse processes (105a, 105b) and a spinous process (107). A disc (108) is located between the superior vertebral body (100) and the inferior vertebral body (102). The spinal cord (110) extends through a central passage formed by the spinal column, and nerve roots (112) transverse the foramenal space (114) defined by the pair of vertebral bodies.

When the disc is damaged due to trauma, disease, or other disorder, the superior vertebral body (100) and inferior vertebral body (102) tend to collapse upon each other, thereby decreasing the amount of space formed by the foramen (114). This result also commonly occurs when the vertebral bodies are afflicted with disease or are fractured or otherwise damaged. When the foramenal space is decreased, the vertebral bodies (100, 102) may impinge upon the nerve root (112), causing discomfort, pain, and possible damage to the nerve root. The foramenal spacers described herein are intended to alleviate this problem by maintaining the foramenal opening and otherwise protecting the nerve root from impingement by the vertebral bodies.

Figure 2A:
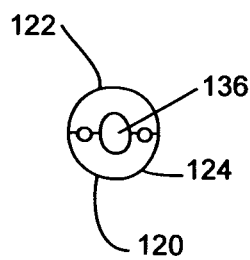
FIGS. 2A-G are illustrations of foramenal spacers.
Figure 2B:
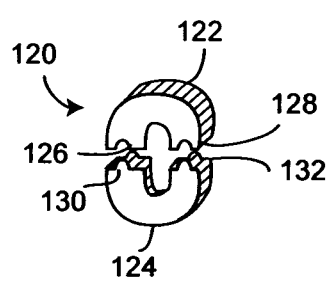
Figure 2C:
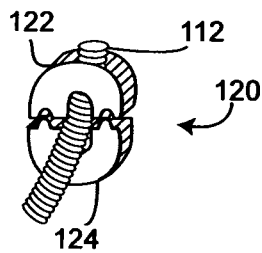
Figure 2D:
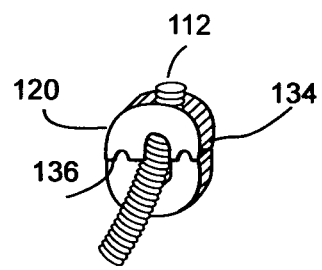

Turning to FIGS. 2A through 2G, several foramenal spacer embodiments are shown. In a first embodiment, shown in FIGS. 2A-D, the foramenal spacer (120) includes a pair of C-shaped members (122, 124). The C-shaped members may include an attachment mechanism or mating surfaces. For example, as shown in FIG. 2B, one C-shaped member (122) includes a groove or notch (126) on each of its inferior-facing surfaces (128), and the other C-shaped member (124) includes a mating tab (130) on each of its superior-facing surfaces (132). Alternatively, the tabs and notches may be alternated, one on one member and one on the other. Other attachment features may be employed, such as a snap-fit mechanism or other similar structure. Of course, the mating surfaces (128, 132) may simply butt up against one another to form a butt-joint that prevents collapse of the foramenal space. In any case, the pair of C-shaped members (122, 124) define a generally disc-shaped member (134) having a central through-hole (136). The central through-hole (136) has a size and shape suitable for passage of nerve root (112) without impingement as shown, for example, in FIGS. 2C and 2D.

Figure 2E:
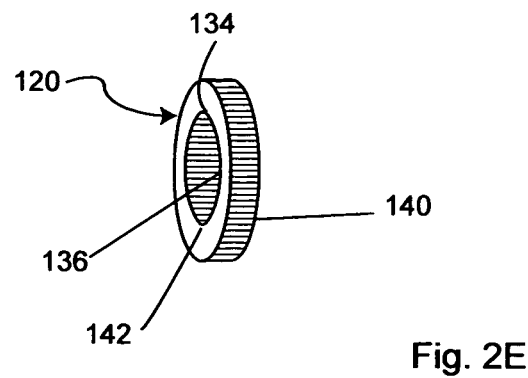

Turning to FIG. 2E, the foramenal spacer (120) may be provided with an outer layer (140) that includes a coating of a soft, conformable material. The outer layer (140) may cover all of the external-facing surfaces of the foramenal spacer (120), and particularly those that are positioned to engage the vertebral body surfaces. The outer layer (140) may comprise a soft, conformable biocompatible material such as silicone, polyurethane, or other similar polymeric materials. The outer layer (140) helps to provide structural protection to the vertebral bodies forming the foramenal space, and also allows the foramenal spacer (120) to adapt to the varying foramenal geometries formed by the vertebral bodies.

An optional inner layer or liner (142) may be provided on the exposed surfaces defining the through-hole (136) of a coating of soft and/or low-friction material to provide an atraumatic surface for passage of the nerve root (112). The inner layer or liner (142) may comprise the materials similar to those used for the outer layer (140). Alternatively, the inner layer or liner (142) may comprise a coating of lubricious materials such as polyethylene, PTFE, or other similar material.

In addition, an optional spring member, gasket, cushion, or other similar material or device (not shown in the drawings) may be interposed between the two C-shaped members (122, 124). Preferably, the spring member (or the like) may be located between the abutting surfaces of the two C-shaped members. This spring member (or the like) expands the spacer (120) with as the spring member extends and compresses, thereby providing a range of motion for supporting the foramenal space.

Figure 2F:
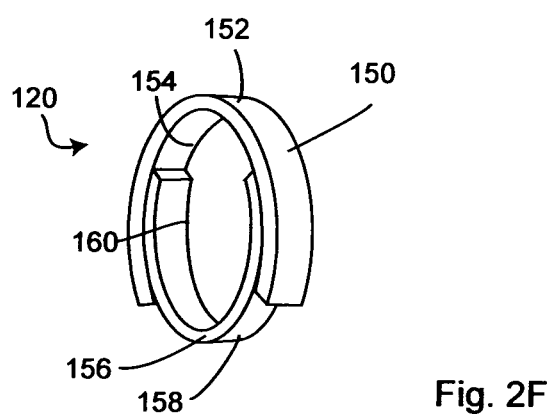

FIG. 2F shows a variation of our foramenal spacer. The foramenal spacer (120) includes a first segment (150) and a second (or inner) segment (156). The first segment (150) includes an external surface (152) that has a shape suitable for engaging the portion of a vertebral body defining the foramenal space (114). Similarly, the other segment (156) includes an external surface (158) that has a shape adapted to engage a portion of the adjoining vertebral body defining the foramenal space (114). An internal surface (154) of the first segment (150) includes a curved portion that rotatably engages a mating curved portion of the external surface (158) of segment (156). In this way, the segments (150, 152) are rotationally connected to one another, i.e., the segments (150, 152) function similarly to a bearing having a center of rotation. When the first segment (150) and second segments (152) are implanted into the foramenal space between vertebral bodies (100, 102), the foramenal spacer (120) allows the two vertebral bodies to pivot relative to one another, thereby providing an additional range of motion. The foramenal spacer (120) shown in FIG. 2F may also include an outer layer (140) and an inner layer or liner (142) described above in relation to FIG. 2E.

Figure 2G:
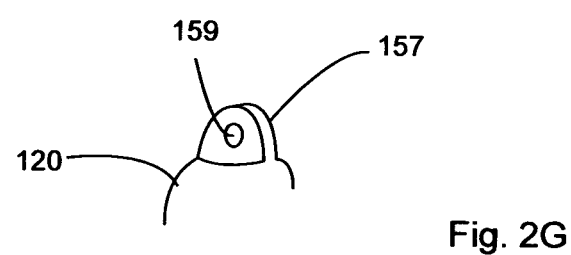

The foramenal spacer (120) may be implanted by any appropriate surgical technique, including accessing the foramenal space by either a posterior approach or a lateral approach. The lateral approach is believed to provide optimal access for exposure of the foramen, but techniques for posterior lumbar interbody fusion (PLIF) and transforamenal lumbar interbody fusion (TLIF) also provide sufficient access. Once access is gained, the foramenal spacer (120) is attached to the pedicle or other anatomic structure that allows extension of the spacer into the foramenal space (114). Depending upon the specific design of the device, the foramenal spacer (120) may be press fit into the foramen (116). FIG. 2G shows a foramenal spacer (120) having a tab (157) with an opening (159) for attaching the foramenal spacer (120) to the pedicle or other anatomical structure.

Figure 3:
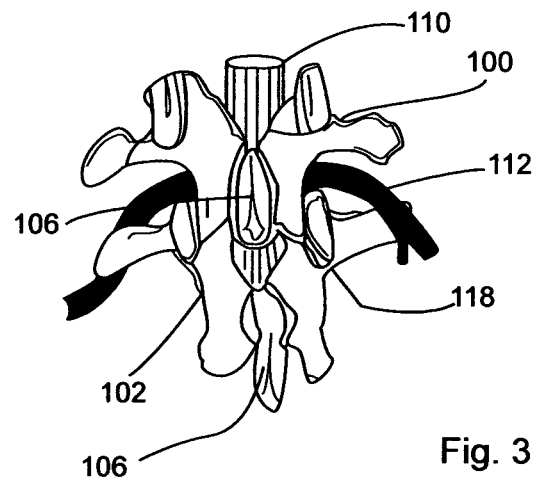
FIG. 3 is a posterior view of a pair of adjacent vertebral bodies, including representations of the facets and facet joints.

Turning next to FIG. 3, a posterior view of a pair of adjacent vertebral bodies is shown. The Figures illustrates a superior vertebral body (100) and an inferior vertebral body (102). Each vertebral body includes a pair of transverse processes (104*a-b* and a spinous process (106) extending generally posteriorly from each vertebral body (100, 102). The spinal cord (110) extends through a central passage formed by the spinal column, and nerve roots (112) transverse the foramenal space (114) defined by the pair of vertebral bodies. A facet joint (118) is formed by a pair of facing facets, one each from the superior and inferior vertebral bodies.

Several of the known devices and systems for posterior spinal stabilization are designed and provide the function of opening the foramen or maintaining the foramenal spacing in order to off-load the nerve that traverses the foramen. This is commonly done by attaching a device to the pedicles of each of the vertebral bodies and providing a distracting force between the attachment members. Several alternative and novel devices and methods are described herein.

Figure 4:
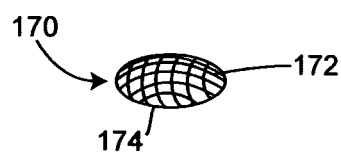
FIG. 4 is a perspective view of an embodiment of a facet joint stabilizing member.

FIG. 4 shows a facet stabilizing member (170). The facet stabilizing member (170) preferably includes a core member (172) encased in a jacket (174). The core member (172) may comprise a hydrogel, gel, elastomer, polyurethane, or other polymeric material suitable for providing the shock absorbing and spacing functions necessary to stabilize the facet joint. The jacket (174) may be a fabric (woven or unwoven) of biocompatible material and is intended to maintain the integrity and shape of the core member (172) and to otherwise provide structural strength to the facet stabilizing member (170). The facet stabilizing member (170) has a size and shape suitable for placement in the facet joint (118) and provide stabilization to the joint and to prevent collapse of the foramenal space.

Figure 5:
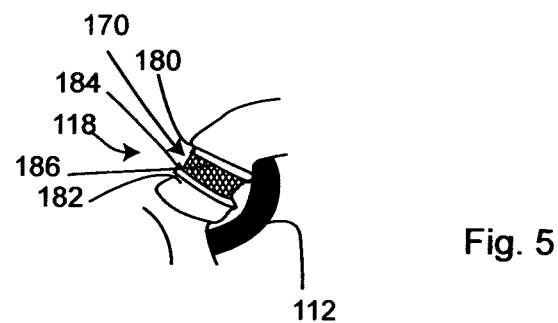
FIG. 5 is a side view of another embodiment of a facet joint stabilizing member shown implanted in a facet joint.

FIG. 5 shows another variation of our facet stabilizing member (170). The depicted spinal stabilizing member (170) includes an upper endplate (180), a lower endplate (182), and a core member (184) extending between and interconnecting the upper endplate (180) and lower endplate (182). The facet stabilizing member also includes a plurality of fibers (186) wound between and interconnecting the upper endplate (180) and lower endplate (182). The construction and materials of the facet stabilizing member (170) shown in FIG. 5 are similar to the construction and materials of the prosthetic intervertebral disc described below in relation to FIG. 18, and to several of the prosthetic intervertebral discs described in U.S. patent application Ser. No. 10/903,276, filed Jul. 30, 2004, and U.S. Provisional Application Ser. No. 60/713,671, filed Sep. 1, 2005, each of which is incorporated by reference. Other prosthetic disc constructions as described in the foregoing applications are also suitable for use in the facet stabilizing members (170) described herein. The size of the facet stabilizing member (170) is typically smaller than the sizes of the prosthetic discs described in the foregoing applications, but the overall construction of the structure may be the same.

The facet stabilizing member (170) is implanted between the pair of opposed facets associated with the pair of adjacent vertebral bodies. Additional features, such as fins, fixation members, or other structures (not shown), may also be incorporated on the facet stabilizing member (170) to limit movement. The facet joint is synovial; implantation may be performed through the capsule. Access to the facet joint may be obtained by any of the methods described above in relation to implantation of the foramenal spacer.

Figure 6A:
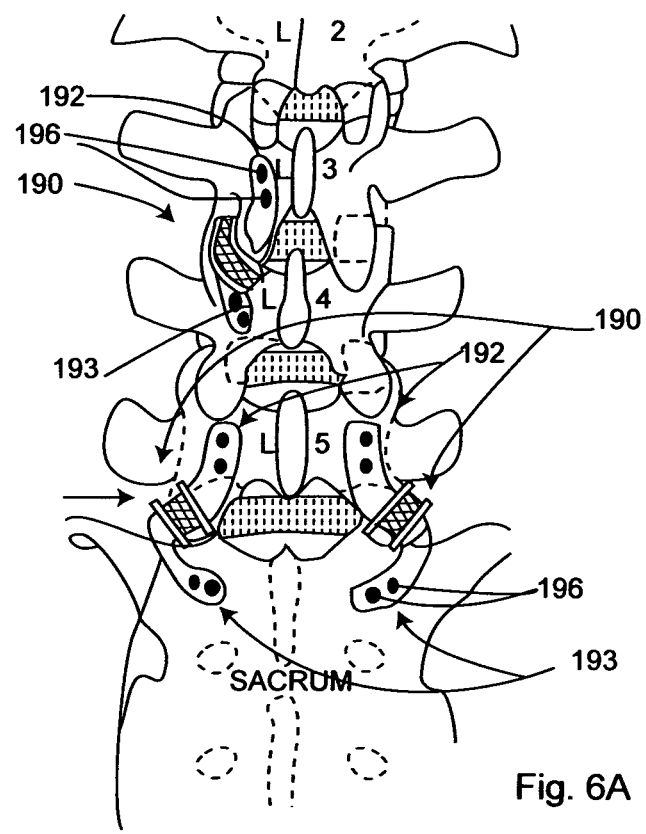
FIG. 6A is a view of a number of prosthetic facets and facet joints implanted upon a spine.
Figure 6B:
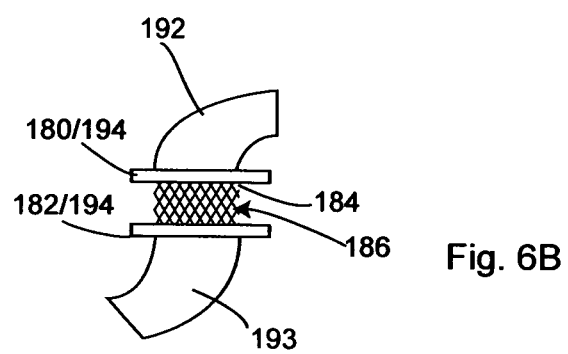
FIG. 6B is a partial side view of a prosthetic facet and facet joint assembly.
Figure 6C:
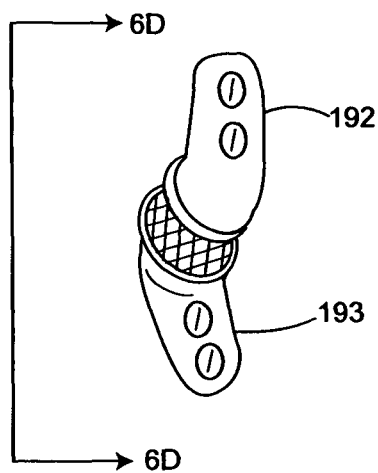
FIGS. 6C and 6D are front and side views of a prosthetic facet and facet joint assembly.
Figure 6D:
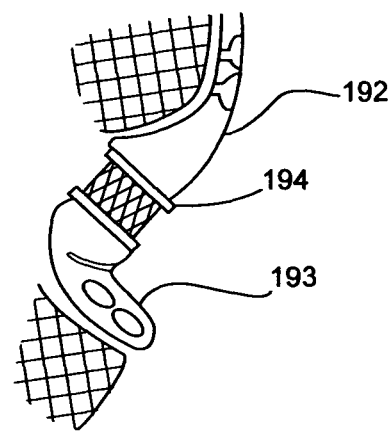
Figure 7:
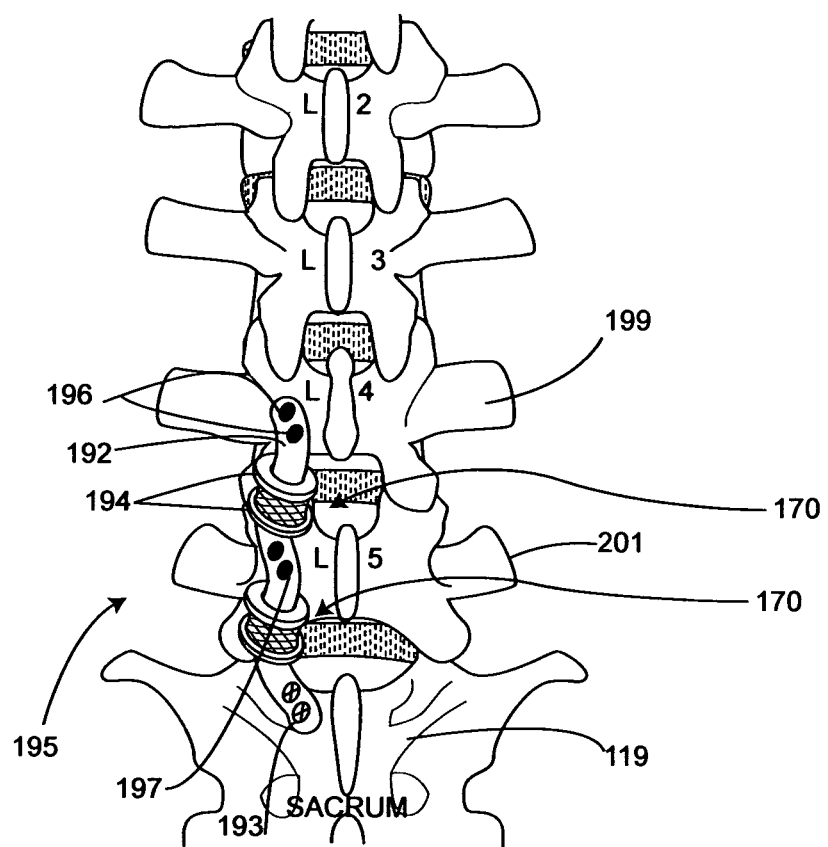
FIG. 7 is an illustration of a portion of a spinal column with a prosthetic facet and facet joint assembly having a pair of prosthetic facet joints.

FIGS. 6A to 7 shows several variations of our prosthetic facet and facet joint assemblies. These assemblies are particularly useful in repairing spinal structure compromised, e.g., during spinal surgical procedures, particularly those including approach by the posterior, where some of or the entire facet is removed to implant one or more prosthetic structures. The devices are similarly suitable in cases where the facets or facet joints are damaged through trauma, disease, or other disorder to stabilize to the effected spinal segments.

FIG. 6A shows a number of combination prosthetic facet and facet joint assemblies (190) implanted in several locations on a spinal column. The native facet and facet joint is removed prior to implanting the prosthetic assembly. Each depicted prosthetic facet assembly (190) includes an upper attachment arm (192) that, as may be seen in the side view of FIG. 6D, is generally elongated and curved forward to match the shape and structure of the prepared native facet. The depicted upper attachment arm (192) is attached to or terminates in an endplate (194) forming a portion of a facet stabilizing member (170). The upper attachment arm (192) is attached to its associated vertebral body by appropriate fasteners, e.g., one or more screws (196). The facet stabilizing member (170) may be similar in construction and materials of construction to those described above in relation to the FIG. 5, above. The assembly (190) also includes a lower attachment arm (193) that is also generally elongated and curved rearward (again, as seen in the side view of FIG. 6D) to match the shape and conform to the structure of the prepared native facet on the lower vertebral body.

The facet stabilizing member (170) is interposed between a pair of prosthetic facets (190, 193) with the facet endplates (194) serving as the endplates for the facet stabilizing member (170). (See, in particular, FIG. 6B). In general, in designing a specific combination prosthetic facet and facet joint assembly (190), the facet stabilizing member (170) is sized and oriented with respect to the prosthetic facets (190, 193) to approach several physical parameters of the facet joint that has been removed. Those parameters include: compressibility, increasing compressibility rate as a function of compression, the ability to limit local spinal rotation to a certain small value, and the ability to rotate in a range of normal values without causing an abnormal or unacceptable rotational movement in the adjacent joints. As shown in FIG. 6A, the facet stabilizing member (170) is generally oriented with respect to the prosthetic facets (190, 193) so that it matches or approaches the orientation of the native facet joint with respect to the respective vertebrae. Obviously, the orientation of combination prosthetic facet and facet joint assembly (190) and its included facet stabilizing member (170) is different for each facet site on the spine. Often, the combination prosthetic facet and facet joint assemblies (190) are implanted in matching (mirror image) pairs on each side of a vertebral body to assure conforming performance.

FIG. 7 illustrates a multi-level stabilization assembly (195) having prosthetic facets and facet joints. The assembly (195) extends over several adjacent vertebral segments using several facet stabilizing members (170). The depicted assembly (195) includes an elongated lower attachment arm (193) that is curved rearward to match the shape and conform to the structure of the prepared site on the sacrum (119). The assembly (195) also includes an elongated upper attachment arm (192) that is curved rearward to match the shape and conform to the structure of the prepared site on the uppermost vertebrae (199), shown as the L-4 vertebra in the drawing. Included in this assembly is a double-ended mid-attachment member (197) that serves to connect the two facet stabilizing members (170), the mid-vertebra (201) or L-5, and indirectly through the two facet stabilizing members (170), lower attachment arm (193) and the upper attachment arm (192). The native facets and associated facet joints would be removed prior to the implantation of the multi-level stabilization assembly (195). Again, a pair of mirror-image multi-level stabilization assemblies (195) would be a desirable implantation choice.

FIG. 8 shows a lateral stabilization device (200) having an upper attachment arm (202a) attached to a superior vertebral body (100) by one or more fasteners, e.g., screws (204), and a lower attachment arm (202b) attached to an inferior vertebral body (102) by one or more fasteners, such as screws (204). The device also includes a stabilization member (206). The stabilization member (206) may include a spring or springs, a damper, or other mechanism that provides a desired stabilization function. The stabilization member may comprise a structure such as the facet stabilization member (170) described above in relation to FIGS. 6A to 7 above.

Our lateral stabilization device (200) may be attached to the lateral surfaces of two adjacent vertebral bodies (100, 102). For assurance of balanced response to spine motion, a pair of lateral stabilization devices (200) may be attached, one on each lateral side of the pair of vertebral bodies.

FIG. 9A shows a pair of adjacent vertebral bodies (100, 102) having both a posterior stabilization device (210) and an anterior stabilization device (220) attached to each of the pair of vertebral bodies. The posterior stabilization device (210) includes a pair of studs or pedicle screws (212), one attached to each of the superior vertebral body (100) and to the inferior vertebral body (102). A stabilization member (214) extends between and interconnects the pair of pedicle screws (212). The stabilization member (214) may comprise a load bearing dynamic structure comprising a spring or springs, one or more dampers (damping in either or both axial directions), or any combination of such structures. The anterior stabilization device (220) includes an anterior element (222), shown in isolation in FIG. 9B. The anterior element (222) may comprise a material having superelastic properties, e.g., nitinol or the like. It may be of a shape that allows the anterior element (222) to be constrained for a minimally invasive implantation procedure.

As shown, the anterior element (222) includes an attachment hole (224) at each end, and a central portion (226) that includes a pair of side bands (228a, 228b) that define a central aperture (230). The anterior element (222) may be rolled or compressed into a low profile contracted state for implantation. Once introduced, the anterior element is partially released from the contracted state and attached to the pair of vertebral bodies (100, 102) adjacent to the damaged disc (108). The anterior element (222) may be attached by fasteners, such as screws or other suitable mechanisms. Once attached, the anterior element (222) is fully extended to its operative state and is capable of bearing loads to stabilize the vertebral segments.

The anterior stabilization device (220) may be used alone, in combination with the posterior stabilization device (210) illustrated in FIG. 9A, or in combination with any other suitable stabilization device or structure. By using a combination of stabilization devices, the amounts and types of stabilization and unloading of the vertebral segment may be tailored to suit a specific clinical situation in a way that may be may not be readily possible using a single stabilization structure.

FIGS. 10A-D show several variations of a posterior dynamic stabilization system made up, in general, of a posterior spacer and one or more restrictor bands. As explained below, the spacer may be integrated with the restrictor bands, or it may be provided independently of the restrictor bands.

Figure 10D:
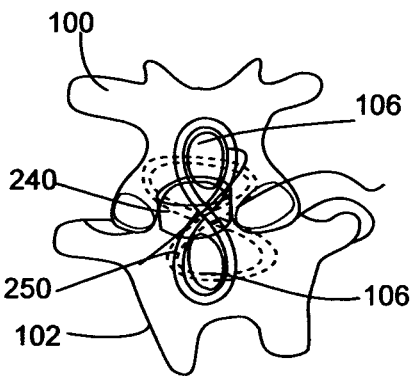
Figure 10D:
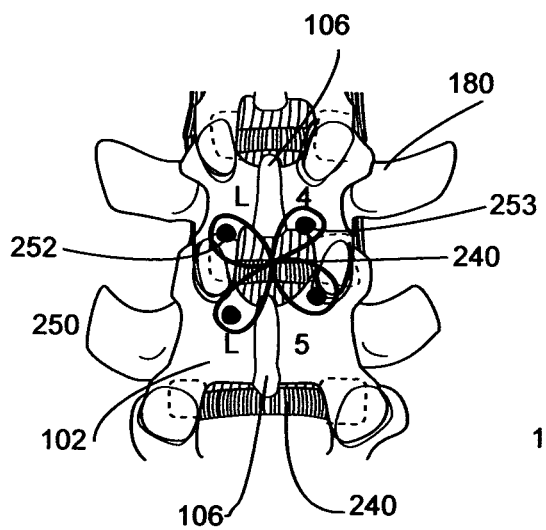
Figure 10D:
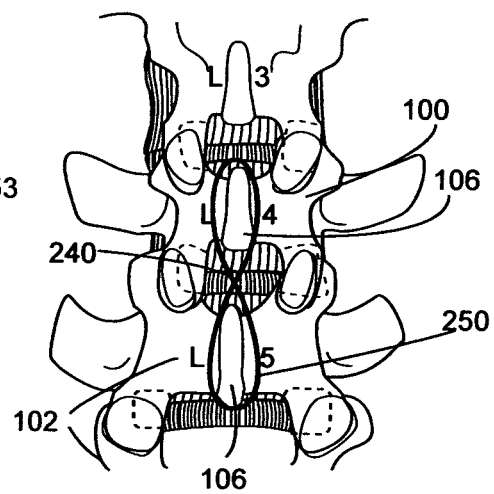

FIG. 10A shows a posterior spacer (240) that is generally in the shape of a short cylinder or bead, having a central through-hole (242) and an upper surface (244) and lower surface (246). The posterior spacer (240) may be designed in other forms or shapes, as is described more fully below. The spacer (240) may comprise a generally compliant biocompatible material, e.g., polymeric materials such as polyurethanes, silicones, TPE's, and other elastomers, or other suitable polymeric material. As shown in the posterior view found in FIGS. 10B1, 10C1, and 10D, the spacer (240) is placed between the spinous processes (106) of a pair of adjacent vertebral bodies (100, 102). The spacer (240) maintains the spacing between the vertebral bodies while allowing a desired amount of relative motion between the two vertebral bodies.

The restrictor band (250) may be a continuous loop and may comprise a relatively elastic biocompatible material, such as any number of elastomeric and/or polymeric materials suitable for the purpose. Should a constrained motion be desired, the loops may be a comparatively inelastic material, e.g., nitinol or other such biocompatible alloys. The restrictor bands (250) are linked to the posterior spine to provide both stability and compliance. The bands (250) may be attached to the vertebra by suitable fasteners, e.g., attachment screws (252) or studs or the like.

FIGS. 10B2 and 10C2 show the spacer (240) and the routing of the bands (250) through the center opening (242) in the spacer. These drawings are provided to show that same routing in isolation from the spine; the same configuration is shown respectively in FIGS. 10B1 and 10C1.

FIG. 10D shows attachment of the bands (250) by looping them directly onto the spinous processes (106) of the pair of vertebral bodies. The materials, sizes, structures, and routing of the restrictor bands (250) may be chosen to tailor a desired type and degree of constraint. For example, a routing pattern that is oriented relatively more diagonally to the axis of the spine, as in FIG. 10C1, will provide more resistance to torsional movement than will a routing pattern that is oriented more vertically, as is shown in FIG. 10D.

Figure 11:
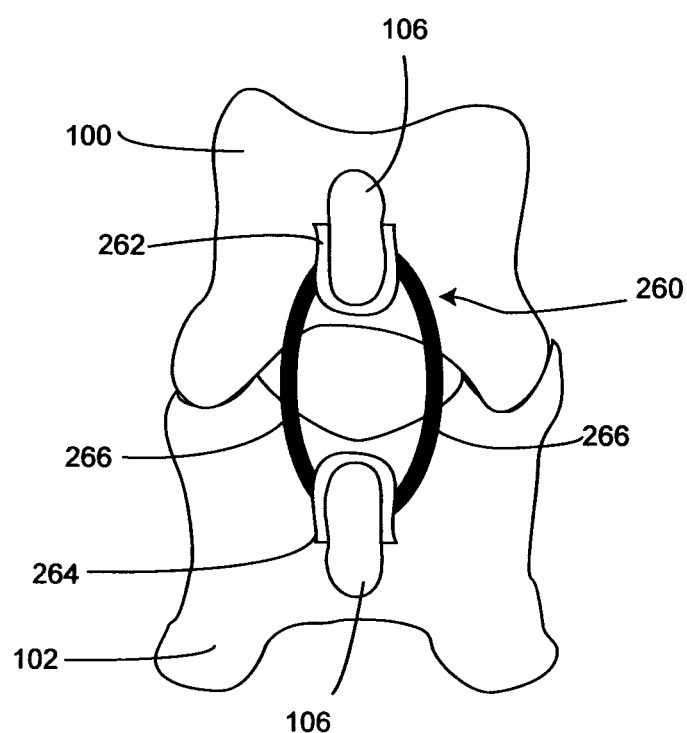
FIG. 11 is a posterior view of another dynamic stabilization system.

FIG. 11 shows another variation of a dynamic spinal stabilization device having the capability of being adjusted after implantation. The illustrated spinal stabilization device (260) includes an upper attachment member (262) and a lower attachment member (264), for attachment to a superior vertebral body (100) and an inferior vertebral body (102), respectively. The two attachment members (262, 264) may be attached to the spinous processes (106) of the respective vertebral bodies (100, 102), as shown, or attached to the pedicles or to other suitable portions of the vertebral bodies. The attachment members (262, 264) may utilize or comprise screws, although other attachment members may be used as desired or as suitable. The stabilization device (260) includes one or more spring elements (266) that each extend between and interconnect the upper attachment member (262) and the lower attachment member (264). Each spring element (266) is may be formed of a suitable biocompatible shape memory or superelastic material, such as nitinol. If the proper alloy is chosen, e.g., by utilizing nitinol having $A_f \geq 100°$ F., the shape and properties of each spring element (266) may be altered after implantation by heating the spring element, for example, using an electric current. Obviously, in such a situation, the spring elements may also be altered prior to implantation. The shape memory material may be trained by a heating process to conform to a predetermined shape upon being heated to a predetermined temperature. For example, leads may be placed in contact with the spring elements (266) under X-ray or other guidance after implantation in the spine of a patient. Electric current is then supplied to the spring elements (266) through the leads, allowing the user to alter the size, shape, or performance characteristics of the spring elements.

Although the spring elements (266) shown in the embodiment illustrated in FIG. 11 are depicted as generally straight struts, the spring elements (266) may have other shapes, sizes, or orientations suitable for a given application.

FIG. 12A is a schematic representation of another spinal stabilization device that transfers loads from one segment of the spine to adjacent segments. Three adjacent vertebral bodies (270, 272, 274) are shown schematically in the Figure. A pair of interconnected stabilization devices (276) are attached to each of the three vertebral bodies. In essence, the stabilization devices (276) are elongate and fairly stiff but include shock absorption and spring providing features in the linkages (280). Each depicted stabilization device (276) includes three fixed rotatable elements (278), each attached to a vertebral body through a bone fixation device or member, e.g., a threaded stud or pedicle screw, and includes a linkages (280) extending between and attached to each adjacent pair of fixed rotatable elements (278).

Each of the fixed rotatable elements (278) comprises a bearing structure (279 in FIG. 12D) or similar mechanism that allows rotation of the attached linkage (280). The depicted bearing structures (279) are often known as Heim joints. This allows a first vertebral segment, such as vertebral body (270), to be loaded in reaction to a load placed upon the adjacent vertebral segments, such as vertebral bodies (272) and (274). As a non-limiting example, when the lowest vertebral body (274) moves to the right, as shown by arrow "A", the transfer of this load through rotation of the fixation elements (278) imposing loading upon the attached linkages (280) influences the upper vertebral body (270) to move to the left, as shown by arrow "B". This movement is consistent with the natural movement of the spine when the body twists. Compression and flexion loads are transferred in a similar manner.

As noted above, each of the fixation elements (278) may include a bearing or similar rotatable structure (279) that allows rotational movement as represented by the arrows "C". This motion transfer is seen from the side in schematic FIG. 12E and from the top in FIG. 12F. The linkages (280) may comprise a compressible element and spring element or elements having a size, shape, spring constant, and other characteristics that provide the desired amount of load transfer in response to rotation of the fixation elements (278). In addition, although two stabilization devices (276) are shown in the Figures, more or fewer devices may be used depending upon the degree of stabilization needed or desired. The stabilization devices (276) may also extend between more (e.g., four or more) or fewer (e.g., two) adjacent vertebral segments.

Figures 13A, 13B:
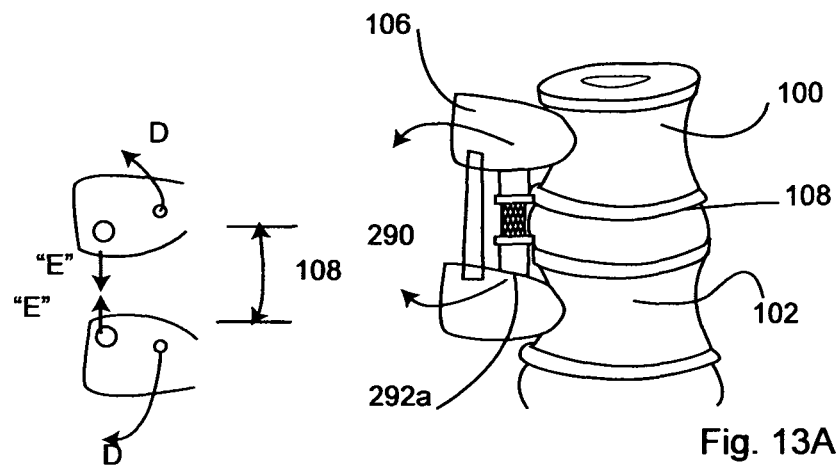
FIG. 13A is a side view of another dynamic stabilization system.
FIG. 13B is a schematic showing rotation and reaction when the FIG. 13A device is deployed.

FIG. 13A shows a multi-component dynamic stabilization system. Current dynamic spinal stabilization systems are typically either interspinous devices (i.e., connected between the spinous processes of adjacent vertebral bodies) or pedicle screw based devices (i.e., connected between pedicle screws attached to the pedicles of adjacent vertebral bodies). Each of these types of dynamic stabilization devices functions by providing a distracting force that unloads the disc (108). FIG. 13A shows an interspinous stabilization system (290) connected to the spinous processes (106) of a pair of adjacent vertebral bodies (100, 102), and a pair of pedicle based stabilization systems (292a, 292b) (only one of the pedicle based systems is shown in the Figure) attached by pedicle screws to the pair of adjacent vertebral bodies (100, 102) on each side of the spinous processes. Each of the pedicle based systems (292a, 292b) comprises a spring loaded or other suitable structure that provides a distracting force (arrows "D" in FIG. 13B), that tends to unload the disc (108). The interspinous system (290), on the other hand, includes a spring loaded or other suitable structure that biases the spinous processes (106) of the adjacent vertebral bodies (100, 102) toward one another, as represented by arrows "E" in FIG. 13B. The combined action of the interspinous system (290) and the pedicle based systems (292a, 292b) creates a moment that relieves pressure from the disc (108).

The interspinous system (290) and the pedicle based systems (292a, 292b) shown in FIGS. 13A and 13B may be constructed such that one or more of the systems is externally adjustable, as described, for example, below.

Figure 14:
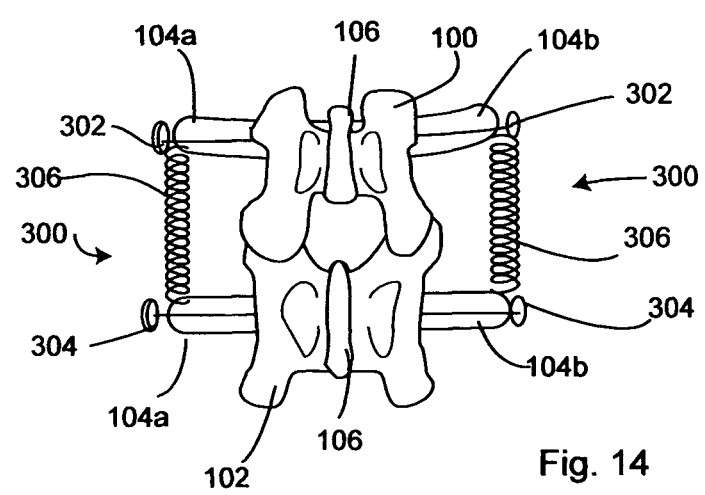
FIG. 14 is a posterior view of another dynamic stabilization system.

FIG. 14 shows a rear view of a pair of adjacent vertebral bodies (100, 102) having dynamic stabilization devices (300) attached to each of the vertebral bodies at a position at or near the transverse processes (104a, 104b) of each vertebral body (100, 102). Each dynamic stabilization device (300) includes an upper attachment screw (302) and a lower attachment screw (304). The screws (302, 304) may be placed through the transverse process to the vertebral body, or they may be attached directly to the vertebral body adjacent the transverse process (104a, 104b). A loading member (306) is attached to each of the upper attachment screw (302) and the lower attachment screw (304) . . . . The loading member (306) stabilizes the adjacent vertebral bodies by providing an appropriate level of distraction or attraction forces. The loading member (306) may comprise a spring, a set of springs, a damping member, or any other suitable structure such as those described elsewhere herein.

Figure 15:
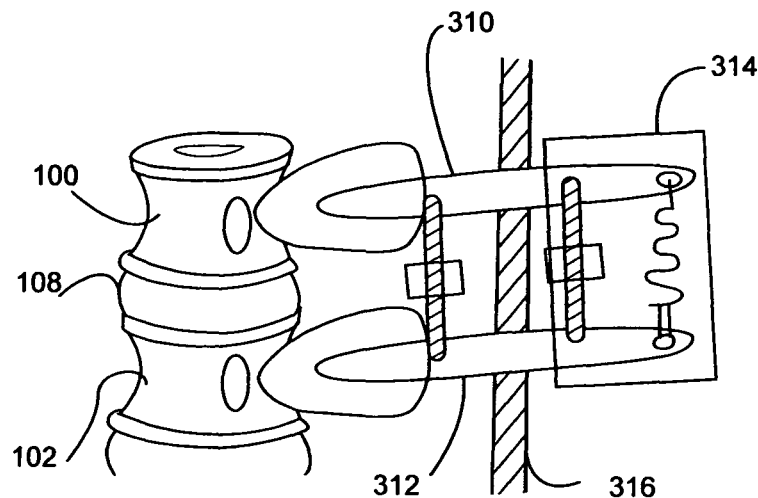
FIG. 15 is a lateral view of another dynamic stabilization system.

FIG. 15 provides a schematic illustration of an externally adjustable dynamic stabilization system. The system includes an upper screw (310) and lower screw (312) extending posteriorly from an upper vertebral body (100) and a lower vertebral body (102), respectively. Each screw extends outside of the patient's body. A stabilization member (314) is attached to each of the screws (310, 312) on the external surface of the patient's back, i.e., outside the surface of the skin (316). The stabilization member (314) may include a spring or springs, dampers (damping in one axial direction, the other direction, or both), The stabilization system (316) may be adjusted post-operatively because it is located externally of the patient without the need for additional surgical intervention.

Figure 16:
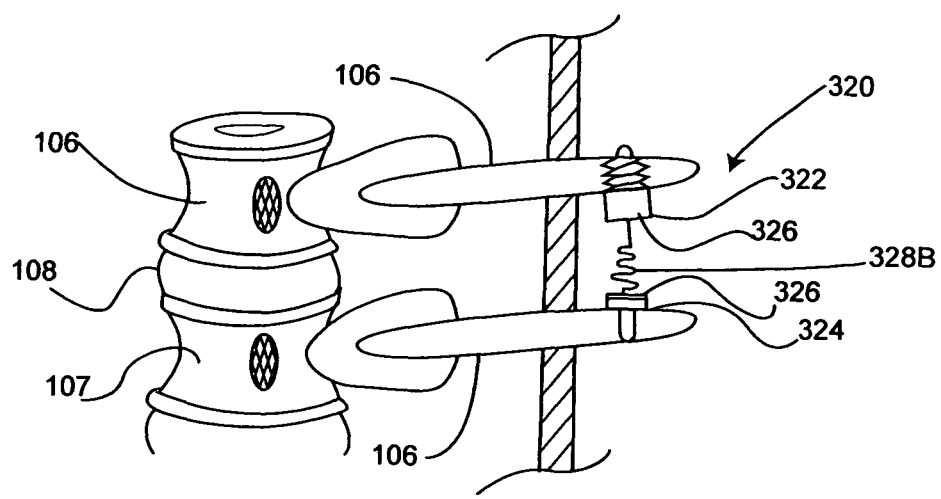
FIG. 16 is a lateral view of another dynamic stabilization system.

FIG. 16 is a schematic illustration of another adjustable stabilization system. The spinal stabilization system (320) includes an upper pot (322) attached to the spinous process (106) of a superior vertebral body (100), and a lower pot (324) attached to the spinous process (106) of an inferior vertebral body (102). Each of the upper pot (322) and lower pot (324) forms a portion of the attachment mechanism for the stabilization device. The upper pot (322) and lower pot (324) may be attached to the spinous processes (106) by any suitable mechanism, such as one or more screws. Each of the upper pot (322) and lower pot (324) includes a cylindrical portion that is adapted to receive a connector (326) located at each of the upper end and lower end of a spring (328). Each of the connectors (326) engages one of the upper pot (322) and lower pot (324), thereby allowing the spring (328) to provide a distracting force to the vertebral bodies (100, 102).

Because the upper pot (322) and lower pot (324) are generally hollow, it is possible to partially fill one or both of the pots (322, 324) to decrease the effective length of the spring (328) extending between the pots, i.e., partially filling the pots causes the connectors to engage the filler material at a level removed from the bottom of the pot (322, 324). Either or both of the pots (322, 324) may be partially filled with bone cement containing polymethylmethacrylate (PMMA) or another suitable material. The filling operation may be performed post-operatively by way of a percutaneous access, thereby eliminating the need for additional surgical intervention.

Figure 17:
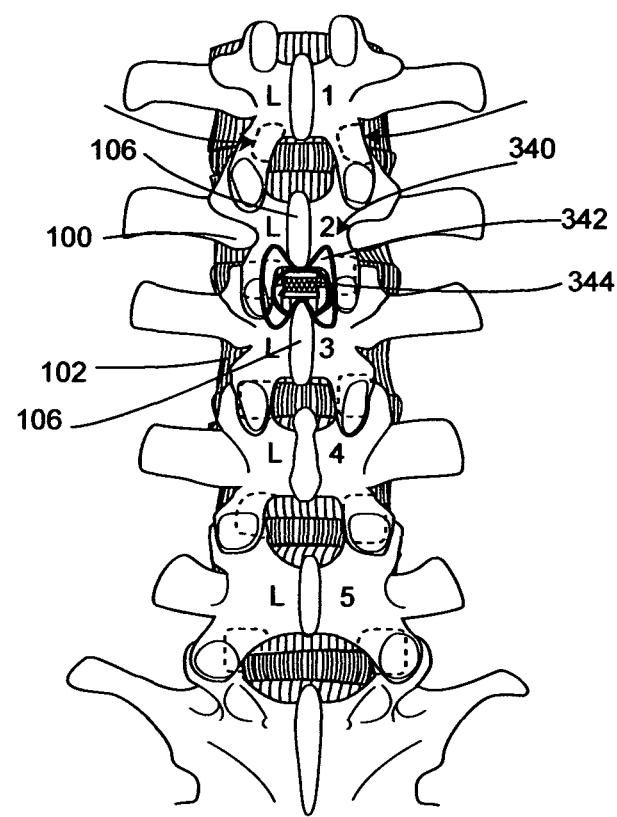
FIG. 17 is a lateral view of another dynamic stabilization system.

FIG. 17 is an illustration of another dynamic stabilization system. The stabilization system (340) comprises a stabilizing disc (344) and an "H" shaped intervertebral spacer (342) including a DIAM™ type intervertebral spacer interposed between the spinous processes (106) of a pair of adjacent vertebral bodies (100, 102). DIAM™ type intervertebral spacers are commercially available and are produced by Medtronic Sofamor Danek. The spacer (342) is generally "H" shaped, including a relatively narrow center section located between relatively wider side sections. This shape allows the spacer (342) to be effectively inserted between the spinous processes (106) of a pair of adjacent vertebral bodies (100, 102), as shown in FIG. 17. The spacer (342) is a silicone device covered with polyethylene, and functions by reducing loading of the disc, restoring the posterior tension band, realigning the facets, and restoring the foramenal height.

In addition, a stabilizing disc (344) is interposed between the spinous processes (106) in place of a portion of the spacer (340). The stabilizing disc (344) has a structure and is constructed in a manner identical to the facet stabilizing member (170) described above in relation to FIG. 5, having a core member located between a pair of endplates. The stabilizing disc (344) allows for compression and rotation, if needed. The stabilizing disc (344) also facilitates lateral bending.

As noted above, this application incorporates by reference U.S. Provisional Patent Application Ser. No. 60/713,671, entitled "Prosthetic Intervertebral Discs," ("the '671 application"), which was filed Sep. 1, 2005, and which is assigned to Spinal Kinetics, Inc., the assignee of the present application. The '671 application describes, inter alias, spinal treatment methods that combine a prosthetic intervertebral disc with a dynamic stabilization system. Each of the dynamic stabilization systems described in the present application are suitable for use in combination with prosthetic intervertebral discs such as those described in the '671 application, and others described in U.S. patent application Ser. No. 10/903,276, filed Jul. 30, 2004, ("the '276 application"), which is also incorporated by reference herein.

Figure 18:
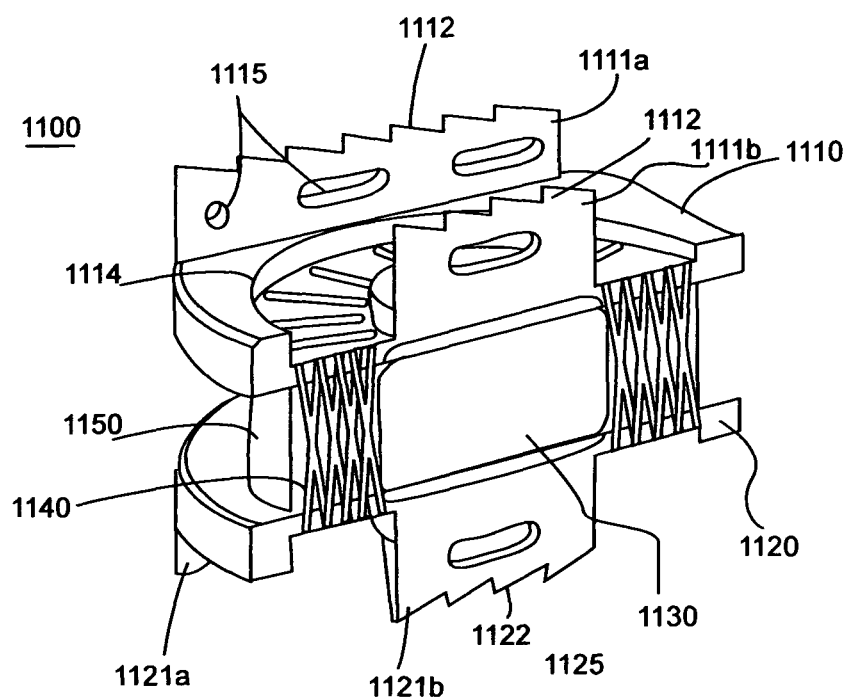
FIG. 18 is a perspective, cross-sectional view of one example of a prosthetic intervertebral disc.

For example, an exemplary prosthetic intervertebral disc (1100) is shown in FIG. 18, which is reproduced from FIG. 3 of the '671 application and which was also described in the '276 application. This prosthetic disc is described for exemplary purposes, and is not intended to represent the only type of prosthetic disc that is suitable for use in combination with the devices and systems described elsewhere herein. Turning to FIG. 18, the prosthetic disc (1100) has an integrated structure that includes an upper endplate (1110), a lower endplate (1120), and a core member (1130) retained between the upper endplate (1110) and the lower endplate (1120). One or more fibers (1140) are wound around the upper and lower endplates to attach the endplates to one another. The wind of the fibers (1140) allows a degree of axial rotation, bending, flexion, and extension by and between the endplates. An annular capsule (1150) is optionally provided in the space between the upper and lower endplates, surrounding the core member (1130) and the fibers (1140). The upper endplate (1110) and lower endplate (1120) are generally flat, planar members, and are fabricated from a biocompatible material that provides substantial rigidity.

The upper surface of the upper endplate (1110) and the lower surface of the lower endplate (1120) are preferably each provided with a mechanism for securing the endplate to the respective opposed surfaces of the upper and lower vertebral bodies between which the prosthetic disc is to be installed. For example, in FIG. 18, the upper endplate (1110) includes a plurality of anchoring fins (1111a, 1111b). The anchoring fins (1111a, 1111b are intended to engage mating grooves that are formed on the surfaces of the upper and lower vertebral bodies to thereby secure the endplate to its respective vertebral body. The anchoring fins (1111a, 1111b) extend generally perpendicularly from the generally planar external surface of the upper endplate (1110), i.e., upward from the upper side of the endplate as shown in FIG. 18. Each of the anchoring fins (1111a, 1111b) has a plurality of serrations (1112) located on the top edge of the anchoring fin. The serrations (1112) are intended to enhance the ability of the anchoring fin to engage the vertebral body and to thereby secure the upper endplate (1110) to the spine.

Similarly, the lower surface of the lower endplate (1120) includes a plurality of anchoring fins (1121a, 1111b). The anchoring fins (1121a, 1111b) on the lower surface of the lower endplate (1120) are identical in structure and function to the anchoring fins (1111a, 1111b) on the upper surface of the upper endplate (1110), with the exception of their location on the prosthetic disc.

The anchoring fins (1111, 1121) may optionally be provided with one or more holes or slots (1115, 1125). The holes or slots help to promote bony ingrowth that assist in anchoring the prosthetic disc (1100) to the vertebral bodies.

The upper endplate (1110) contains a plurality of slots (1114) through which the fibers (1140) may be passed through or wound, as shown. The actual number of slots (1114) contained on the endplate is variable. The purpose of the fibers (1140) is to hold the upper endplate (1110) and lower endplate (1120) together and to limit the range-of-motion to mimic the range-of-motion and torsional and flexural resistance of a natural disc.

The core member (1130) is intended to provide support to and to maintain the relative spacing between the upper endplate (1110) and lower endplate (1120). The core member (1130) is made of a relatively compliant material, for example, polyurethane or silicone, and is typically fabricated by injection molding. A preferred construction for the core member includes a nucleus formed of a hydrogel and an elastomer reinforced fiber annulus. The shape of the core member (1130) is typically generally cylindrical or bean-shaped, although the shape (as well as the materials making up the core member and the core member size) may be varied to obtain desired physical or performance properties. The core member (1130) shape, size, and materials of construction will directly affect the degree of flexion, extension, lateral bending, and axial rotation of the prosthetic disc.

The annular capsule (1150) may be made of polyurethane or silicone or hydrogel and may be fabricated by injection molding, two-part component mixing, or dipping the endplate-core-fiber assembly into a polymer solution. A function of the annular capsule is to act as a barrier that keeps the disc materials (e.g., fiber strands) within the body of the disc, and that keeps natural in-growth outside the disc.

The foregoing prosthetic disc (1100), or other suitable prosthetic discs, may be implanted by surgical techniques described in the '671 and '276 applications and elsewhere. As described above, it may be advantageous to combine the prosthetic intervertebral disc with any of the devices, systems, and methods described herein to obtain synergistic therapeutic results in treatment of spinal disease, trauma, or other disorder.

CONVENTIONS

It is our intention that this description not be limited to the particular described variations. It is also to be understood that the terminology we use is solely for the purpose of describing particulars of the devices and methods. We do not intend the terminology to be limiting, since the scope of the present invention will be limited only by the appended claims.

Where a range of values is provided, we intend our description to specifically include each intervening value, to at least the tenth of the unit of the lower range limit unless the context clearly dictates otherwise, found between the upper and lower range limits of that range and any other stated or intervening value in that stated range.

Unless defined otherwise, we intend all technical and scientific terms to have the same meaning as commonly understood by one of ordinary skill in the art to which the described device and methods belong. All publications mentioned herein are incorporated herein by reference for the purpose of disclosing and describing the methods and/or materials in connection with which the publications are cited.

We intend that in this specification and in the appended claims, the singular forms "a", "an," and "the" include plural referents unless the context clearly dictates otherwise.

As will be apparent to those of skill in the art upon reading this disclosure, each of the described device and method has discrete components and features that may be readily separated from or combined with the features of any of the other several devices and methods.

It is to be understood that the described devices and processes that are the subject of this patent application are not limited to the particular described variations, as such may, of course, vary. In particular, our description is meant to include implanted or implantable combinations of two or more of the specific devices described herein, to the extent that the devices are compatible with one another.

I claim:

1. An inter-spinous process, dynamic stabilizing device interposable between spinous processes associated with a first vertebral body and a second vertebral body adjacent said first vertebral body, said first vertebral and second vertebral bodies having facet joints and foramenal spaces, said device comprising:
   a. upper and lower end plates,
   b. at least one compressible core assembly extending between and interconnecting said upper and lower end plates, said compressible core assembly comprising a compressible core member and a plurality of fibers wound between and interconnecting said upper and lower end plates, wherein the compressible core assembly is configured to stabilize the spacing between the first spinous process and the second spinous process, to provide compressible resistance to compression, and to permit rotation, and to permit lateral bending, and
   c. a spacer including relatively wider side sections and a relatively narrower section, the spacer containing within it said upper and lower end plates and said at least one compressible assembly.

2. The inter-spinous process stabilizer of claim 1 wherein the compressible core member comprises one or more polymeric materials.

3. The inter-spinous process stabilizer of claim 1 wherein the spacer comprises one or more polymeric materials.

4. The inter-spinous process stabilizer of claim 1 wherein the spacer comprises a silicone polymer.

5. The inter-spinous process stabilizer of claim 4 wherein the spacer further comprises a polyethylene covering.

6. The inter-spinous process stabilizer of claim 1 wherein the spacer is configured by sizing such that, when implanted between the first spinous process and the second spinous process restores the posterior tension band, realigns the facets associated with the first vertebral body and the second vertebral body, and to restore the foramenal height associated with the first vertebral body and the second vertebral body.

* * * * *